United States Patent [19]
Virta et al.

[11] Patent Number: 5,050,197
[45] Date of Patent: Sep. 17, 1991

[54] MAMMOGRAPHIC METHODS AND APPARATUSES

[75] Inventors: Arto Virta; Kari Malmén, both of Helsinki; Pekka Strömmer, Espoo, all of Finland

[73] Assignee: Automed Oy, Finland

[21] Appl. No.: 438,460

[22] PCT Filed: May 4, 1989

[86] PCT No.: PCT/FI89/00082
§ 371 Date: Dec. 19, 1989
§ 102(e) Date: Dec. 19, 1989

[87] PCT Pub. No.: WO89/11248
PCT Pub. Date: Nov. 30, 1989

[51] Int. Cl.[5] .............................. A61B 6/04
[52] U.S. Cl. ....................... 378/37; 378/210
[58] Field of Search ........................... 378/37

[56] References Cited
U.S. PATENT DOCUMENTS

| 3,609,355 | 9/1971 | Schwarzer | 250/50 |
| 4,433,690 | 2/1984 | Green et al. | 128/915 |
| 4,599,738 | 7/1986 | Panetta et al. | 378/37 |
| 4,613,982 | 9/1986 | Dornheim et al. | 378/37 |
| 4,727,565 | 2/1988 | Ericson | 378/37 |
| 4,768,516 | 9/1988 | Stoddart et al. | 128/665 |

Primary Examiner—Craig E. Church
Attorney, Agent, or Firm—Steinberg & Raskin

[57] ABSTRACT

Methods and apparatuses in mammographic photography, wherein the breast (M) to be photographed is pressed and spread between holders (6,7) attached to the photographing apparatus. A beam (R) of X-radiation is directed from one side of the holders (6,7) through the breast (M) placed between the holders at depicting means (21) placed at the opposite side of the holders in relation to the source (2) of X-radiation, said depicting means being placed inside a film cassette or equivalent placed in connection with the frame of the apparatus. In order to carry out the photography of a breast ($M_1$; $M_2$; $M_3$) in different projections (f;g;h), the frame part (25) of the apparatus, in which the source (2) of radiation, the depicting means (21), as well as the breast holders (6,7) are fitted, is turned around such an axis (b—b) as substantially coincides with the central axis (a—a) of the breast (M) to be photographed, which is being pressed by the breast holders (6,7). One objective of the invention is that the person who is being photographed should not have to move and that the height position of the apparatus should not have to be altered, at least not to a substantial extent, when the projection or mode of photography is changed.

18 Claims, 6 Drawing Sheets

MAMMOGRAPHIC METHODS AND APPARATUSES

BACKGROUND OF THE INVENTION

The invention concerns methods in mammographic photography, wherein the breast to be photographed is pressed and spread between holders attached to the photographing apparatus, a beam of X-radiation being directed from one side of said holders through the breast placed between the holders at depicting means placed at the opposite side of the holders in relation to the source of X-radiation, the depicting means being placed inside a film cassette or equivalent placed in connection with the frame of the apparatus.

The invention further concerns mammographic apparatuses intended for carrying out the method of the invention, these apparatuses comprising a frame part, on which a turnable frame part is mounted, most preferably as to be turnable around a horizontal axis, and in which frame part a source of radiation and means for holding the film cassette as well as holders for the breast to be photographed, to be placed between the source of radiation and said cassette supporting means, are fitted, which breast holders are displaceable relative one another so as to press the breast to be photographed between said holders.

Mammography means a method of radioscopy of breasts, wherein a roentgenogram is taken of the breasts. In connection with the photographing, the breast is pressed and spread in a way known in the prior art between the holders in the photographing apparatus.

Owing to the nature of the tissue to be photographed, in the photographic method a relatively soft radiation is used, the anode voltage of the X-ray tube being about 20 . . . 28 kV. This results in problems of scattering, which are the more important become more serious, the thicker the tissue to be photographed is. In mammography, it is, however, be important to depict so-called microcalcifications, whose diameters are of an order of 0.1 mm.

As is known in the prior art, in complete mammographic photography, three different projections are used. In mass photography, only one, generally vertical, projection is used.

In addition to the roentgenograms taken in different projections, if necessary, enlarged photographs are taken of suspect locations.

Prior-art apparatuses can also be used for so-called biopsy photographing. Biopsy photography concerns a method wherein the breast is photographed by using a so-called biopsy plate so that the openings in the biopsy plate become visible in the roentgenogram. In biopsy photography, the film is developed while the breast to be photographed is kept in its holders, and the finding, if any, is located with the aid of the holes in the biopsy plate, and with their aid a sample is taken from a suspect location.

By means of the prior-art mammographic methods and apparatuses, it is also possible to take enlarged roentgenograms, which takes place such that a particular stand is placed on the normal breast holder, by means of which said stand the breast to be photographed is placed closer to the focus of the source of radiation. The use of such a separate stand is inconvenient, and, thus, one object of the present invention is to provide a new method and apparatus, wherein said separate stand becomes unnecessary.

In mammography, attempts are made to press the breast as flat as possible, because soft secondary radiation is scattered. The thinner the breast can be made, the less secondary radiation can be scattered. To prevent scattering, lattice solutions of various types are also used.

In respect of the prior art related to the present invention, reference is made by way of example to the mammographic apparatuses known from the following U.S. Pat. Nos. 3,824,297, 3,971,950, 4,097,748, 4,599,738, and 4,613,982.

The prior-art mammographic apparatuses have involved several drawbacks, which are eliminated in certain respects by means of the new solutions of the present invention.

One of the most important drawbacks has consisted of the difficulties in the operation of the prior-art apparatuses, these difficulties including the necessity of the patient ot move and to change her position when the projection or mode of photographing is changed, and it has been necessary to adjust the level of the breast holders in the apparatus between different processes of photography. This has increased the time taken by the photography, which is a considerable drawback in particular in the case of mass photography.

In the prior-art apparatuses, difficulties have also occurred in how to be able to press and to attach the breast to be photographed between the holders in the apparatus in a favorable way. The stage of pressing the breast, which is included in mammography, is often experienced by the patients as quite disagreeable, and as this stage has, in the prior-art apparatuses, often been associated with a necessity to readjust the breast to be photographed in a more advantageous position, this drawback has been experienced as quite embarrassing.

SUMMARY OF THE INVENTION

Thus, an object of the invention is to provide a mammographic apparatus in which the various roentgenograms can be taken without having to shift the patient or to adjust the level of the apparatus when moving from one projection or mode of photography to the other.

A further object of the invention is to provide a mammographic apparatus which can be automated to a very high extent.

In view of achieving the objectives stated above and those that will be hereinafter explained a first mammographic method in accordance with the invention is mainly characterized in that in order to carry out the photography of a breast in different projections, the frame part of the apparatus, in which the source of radiation, the depicting means, as well as the breast holders are fitted, is turned around such an axis as substantially coincides with the central axis of the breast to be photographed, which is being pressed by the breast holders, or which is at the proximity of such axis of the breast, the purpose being that the person who is being photographed does not have to move and the height position of the apparatus does not have to be altered, at least not to a substantial extent, when the projection or mode of photography is changed, and that for photography the breast is pressed against a holder, most appropriately the lower press member, attached to said turnable frame part.

A second mammographic method in accordance with the invention is mainly characterized in that the breast to be photographed is placed on the top face of the lower holder, against which the breast to be photographed is pressed from the root portion of its upper side by means of the outer tip portion of the upper press member, that the upper press member is displaced by pivoting it around its articulation point so that it becomes substantially parallel to the support plane of the lower holder in the frame part that is stationary relative to the source of radiation and the part for holding the depicting means, and that when the upper and lower holders become substantially parallel to one another, if necessary, the pressing of the breast is continued by displacing the upper press member in its linear guides so that it retains its orientation.

A first apparatus in accordance with the invention is mainly characterized in that the lower holder of the breast is fitted in connection with the aforementioned turnable frame part, most preferably in fixed relative thereto, and that said lower holder is placed in such a position relative the axis of rotation of the turnable frame part that, when the breast to be photographed is pressed from above by means of the displaceable upper holder, the central axis of the breast substantially coincides with the axis of rotation of the turnable frame part or is placed at the proximity of the axis of rotation.

A second apparatus in accordance with the invention is mainly characterized in that the upper holder is fitted to be pivotable around an axis substantially perpendicular to the central axis of the breast, so that the breast to be photographed is pressed by means of the outer tip of the upper holder, at the initial stage of the pressing, from above the breast at its root, and that thereupon, when the upper holder is being shifted downwards, it is pivotable around its articulation shaft so that it becomes substantially parallel to the plane of the lower holder.

BRIEF DESCRIPTION OF THE DRAWING

In the following, the invention will be described in detail with reference to the figures in the accompanying drawing while starting from a prior-art solution.

FIGS. 1aa and 1bb show a known embodiment of mammographic apparatus, which illustrates the prior art.

PREFERRED EMBODIMENTS OF THE INVENTION

FIGS. 1aa and 1bb show a prior-art solution of mammographic apparatus, wherein the part 3 that supports the tube head 2 and the depicting means is mounted at its center P of gravity on the vertical frame 4 of the apparatus 1. By means of such an apparatus, the advantage is obtained that the apparatus 1 can be substantially balanced. However, a drawback is that the apparatus 1 requires a locking device. Also, the apparatus of this prior-art solution causes a necessity both to adjust the height and to shift the patient laterally on moving from one projection C, D, E to the other, which makes the photographing slower and more difficult and prevents automation of the apparatus on moving from one projection to the other.

Figure 1:
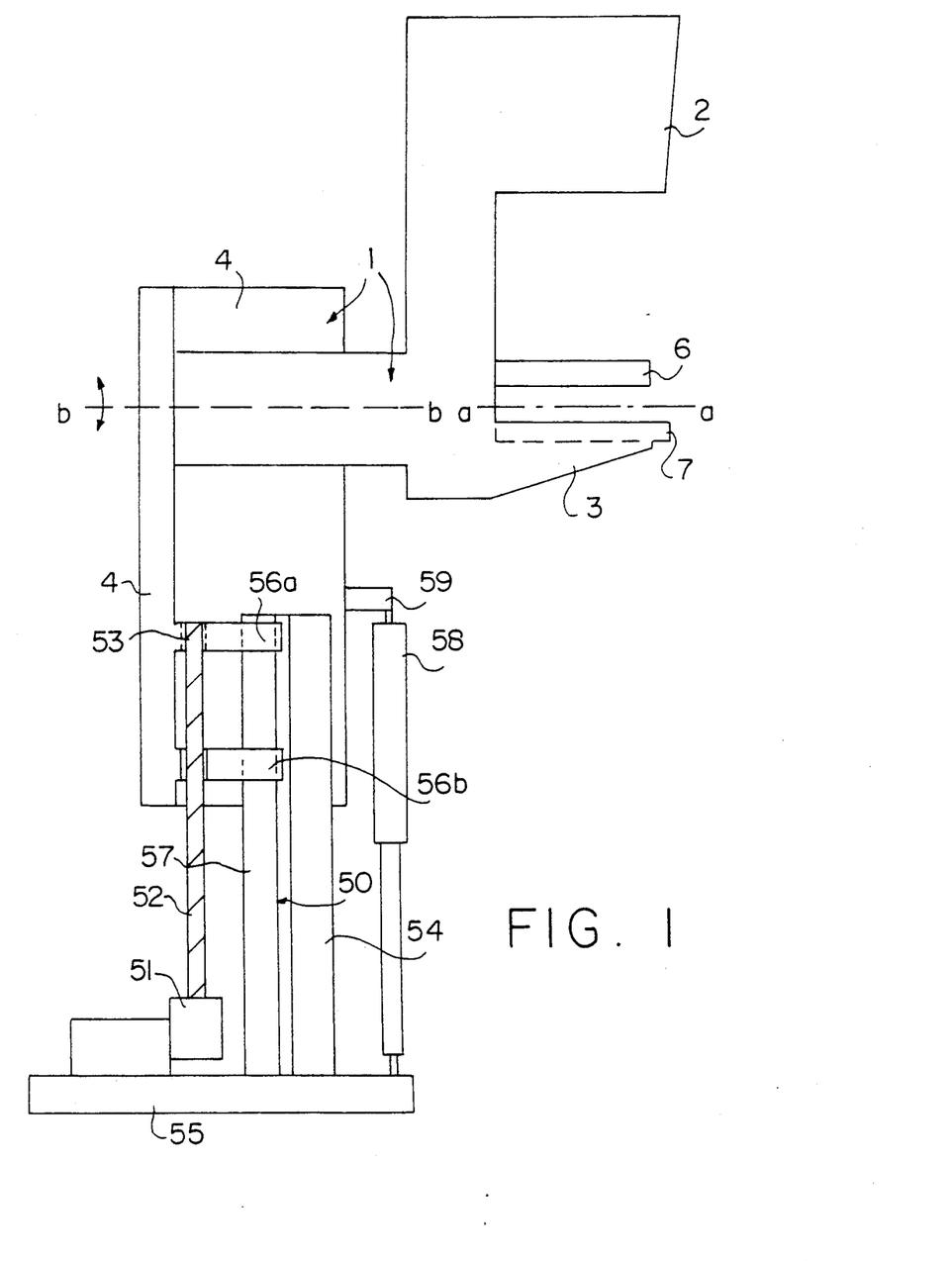
FIG. 1 is a schematical side view of an apparatus in accordance with the invention as a whole.

To start with, referring to FIG. 1, the basic construction of the apparatus 1 in accordance with the invention will be described. The apparatus comprises a vertically displaceable vertical frame 4, to which a part turntable around a horizontal axis b—b is attached, said part comprising the tube head 2 and the press plates 6 and 7 as well as the film holder 3. The vertical frame 4 is arranged to be displaceable in the vertical direction on the frame part 54, said frame part 54 comprising a vertical guide or guides 57. In connection with the vertical guides 57 there are guide casings 56a and 56b, which are fitted around the vertical guides 57. In connection with the pedestal 55 of the apparatus, a motor 51 is fixed, by means of which the transfer screw 52 is rotated. In connection with the threading of the transfer screw 52 there is a threaded part 53, by whose means the frame 4 is displaced vertically. With a view to compensating for the weight of the displaceable frame 4 and of the other parts attached to same, a gas spring 58 is fitted between the frame 4 and the pedestal 55, this gas spring 58 being attached from one of its ends to the displaceable frame 4 by means of a projection part 59.

Figure 1A:
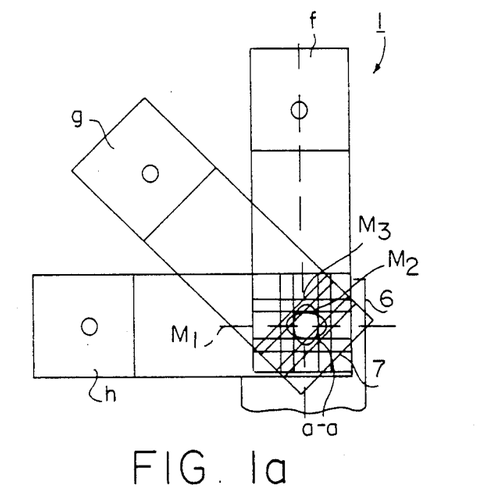
FIGS. 1a and 1b are schematical illustrations of a solution of mammographic equipment from two different projections.
Figure 1B:
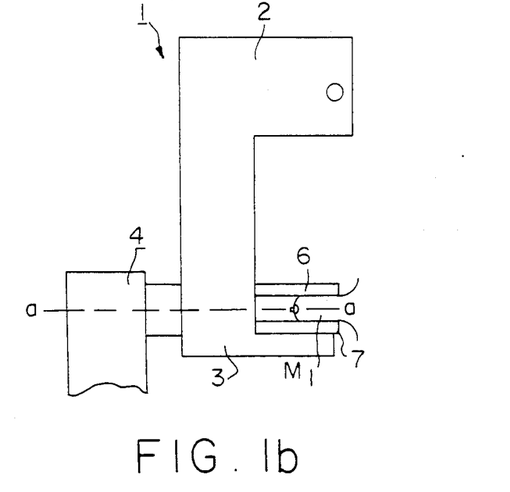

In the apparatus 1 in accordance with FIGS. 1a and 1b, the part 3 that supports the tube head 2 and the depicting means is mounted on the vertical frame 4 of the apparatus 1 at the central axis a—a of the breast $M_1$ that is pressed between the upper press member 6 and the lower press member 7. Thereby the apparatus in accordance with the invention eliminates any necessity for readjusting the apparatus or the position of the patient when moving from one projection f, g, h (different positions $M_1$, $M_2$, and $M_3$ of the breasts) to the other. The apparatus in accordance with the present invention, however, requires particular operations to counterbalance the apparatus (described in more detail in relation to FIG. 3), but these particular operations are reasonable in view of the advantage that is achieved. Moreover, the operation of the apparatus is motorized, so that complete counterbalancing is not indispensable or even needed. Thus, by means of the apparatus of the invention, it is possible to increase the degree of automation.

Figure 2:
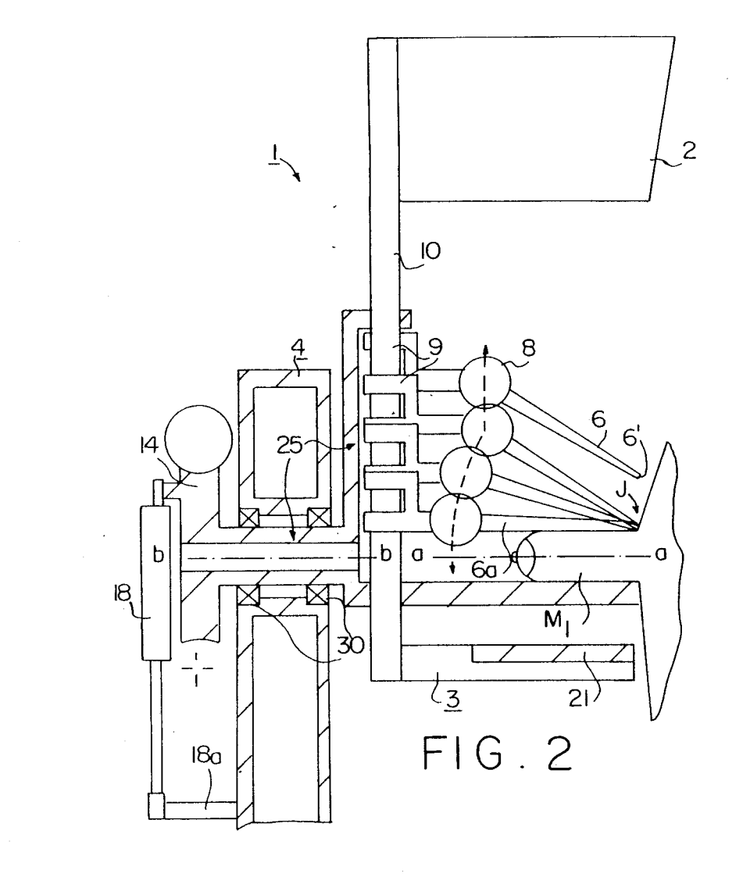
FIG. 2 is a schematical illustration of the shifting of the upper press member into its position in accordance with a preferred embodiment the invention.

In mammography, it is critical that the commonest location of cancer is in the outer upper quarter of the breast close to the body. Thus, it is important that the tissue at the root of the breast is included in the picture. When prior-art apparatuses are used, the nurse spreads the breast from the rear at the initial stage of the pressing of the breast, and thereat, when the upper press member approaches the breast, there remains no space for the hands of the nurse, and she must release her grasp before the press member locks the breast. On the contrary, in the upper press-member embodiment in accordance with the invention, which is shown in FIG. 2, there remains space for the hands of the nurse to spread the breast on the lower press member 7 at the initial stage of the pressing, the tip 6' of the press member 6 locking the press at the end of said initial stage. The upper press member 6 is mounted on the rod 10 by means of a linear journalling 9. Thus, the tip 6' of the downwardly inclined upper press member 6 grasps the breast $M_1$ at its root J, whereinafter the upper press member 6 is pivoted around its tip 6' at the same time as the upper press member 6 moves in its linear journalling 9 along the guide bar 10 and is pivoted around its articulation point 8. The articulation point 8 is provided with an adjustable spring loading, which permits pivoting of the upper press member 6 until it reaches its normal position 6a, i.e. the position parallel to the lower press plate, whereupon the pressing of the breast $M_1$ can be increased further if necessary while the press member 6a retains its orientation.

Figure 3:
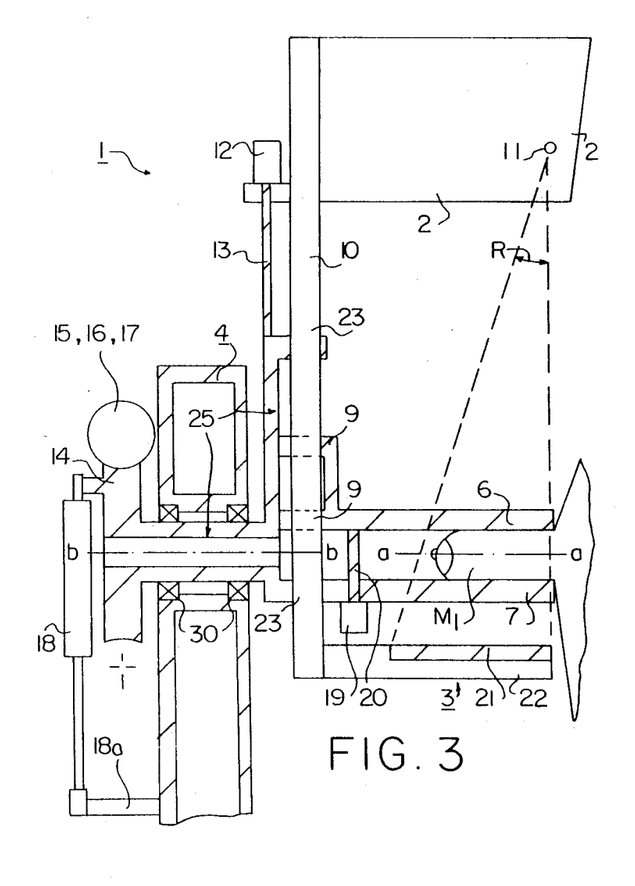
FIG. 3 is a schematical illustration of a mammographic apparatus in accordance with a preferred embodiment of the invention in the situation of removal of the cassette after biopsy photography.

In FIG. 3, the apparatus 1 in accordance with the invention is shown in the position after biopsy photography, corresponding to the removal of the film cassette. Thereat the breast $M_1$ is still pressed between the upper press member 6 and the lower press member 7, but the cassette rack 22 and the tube head 2 have been run slightly downwards by means of the motor 12 and the screw 13 for removal of the cassette 21.

In FIGS. 2 and 3, a revolving part 25 is supported on the vertical frame 4 of the apparatus 1 by means of bearings 30, the part 25 being provided with a stationary lower press plate 7. The film holder 22 itself and the tube head 2 are attached to a common frame part 10, which is mounted by means of a linear journalling 23 on the part 25 revolving around the horizontal axis b—b. In FIG. 3, the upper press member 6 moves relative to the frame part 10 in its journalling 9, and the lower press member 7 is stationary. Thus, without any separate additional elements, it is possible to convert to enlarged photography, even without releasing the pressing. Moreover, by means of a preferred embodiment in accordance with the invention, it is possible to substitute for a biopsy cassette rack.

The vertical frame part 10 is displaced by means of the motor 12 and the screw 13. The revolving part 25 comprises a spiral gear 14, to which a spiral screw 15 as well as a primary gear 16 and a rotating motor 17 are connected. The movement of rotation is counterbalanced by means of a balancing gas spring 18, one of whose ends is connected to the wheel 14 by means of a lever, while the other end is connected to the vertical frame 4 of the apparatus 1 by means of an arm 18a. When moving over to a new projection g, h of photography, the rotation of the part 25 also takes place around the central axis a—a of the breast M, because the axis a—a substantially coincides with the axis b—b of rotation of the part 25. Thus, when the projection of photography is being changed, the necessity of height adjustment of the apparatus 1 is eliminated. The apparatus 1 in accordance with the invention includes readiness for biopsy photography, so that separate installation of an additional part is not necessary when converting to biopsy photography; only the upper press plate 6 must be exchanged. The upper press plate 6 is chosen in accordance with the film size used. The film sizes may be, e.g., 18×24 cm or 24×30 cm. Different types of upper press plates 6 of different sizes are needed for the apparatus 1 in accordance with the invention, for both film sizes, the different plates needed for biopsy photography, as well as the spot photography plates. The upper press plates 6 are made of a material preferably readily penetrable by X-radiation, e.g., so that the transparent part is made of polycarbonate or acrylic and connected to the width-adjustment unit shown in FIG. 9. In this way the press plates can be made simple and inexpensive.

Figure 4:
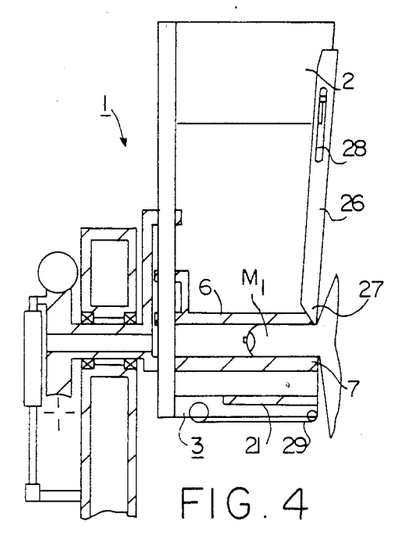
FIG. 4 illustrates the shields used in a mammographic apparatus in accordance with the invention.

FIG. 4 shows the shields used in the device 1 in accordance with the invention. The upper shield 26 is linked 27 with the upper press member 6 and attached by means of its guide groove 28 to the tube head 2. The lower shield curtain 29 is attached to the part 3 that supports the depicting means and to the lower press member 7. The upper shield 26 protects the head and jaw and the shoulders of the person to ba photographed as well as, in the case of obese persons, any extra fatty tissue from the radiation beam R. The lower shield curtain is needed mainly only in enlarged photography to prevent access of fatty tissue of the person to be photographed between the lower press member 6 and the part 3 that supports the depicting means.

Figure 5:
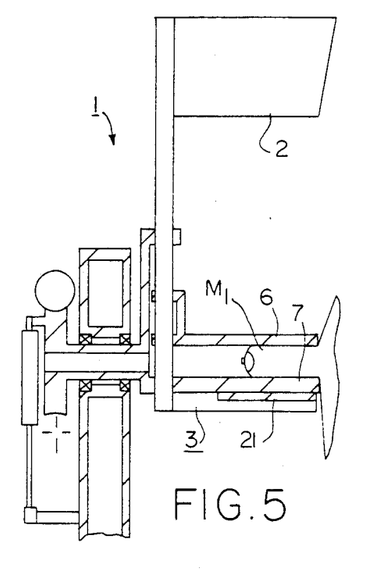
FIG. 5 is a schematical illustration of a mammographic apparatus in accordance with the invention in its position of normal photography.

FIG. 5 shows the apparatus 1 in accordance with the invention in the normal photographing position. In such a case, the lower press plate 7 has been run into contact with the part 3 that supports the depicting means 21. From normal photography it is possible to move over to enlarged photography and to biopsy photography without removing the breast $M_1$ (from between the upper press member 6 and the lower press member 7).

Figure 6:
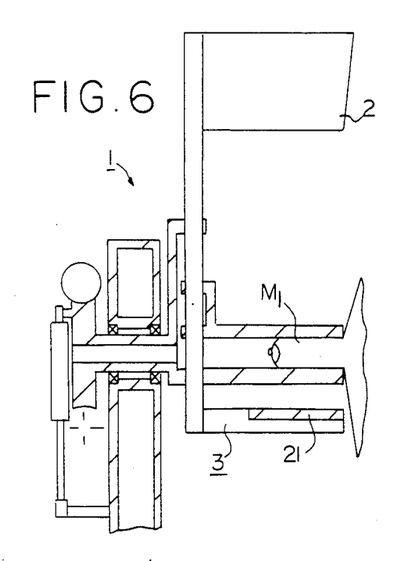
FIG. 6 is a schematical illustration of an apparatus in accordance with the invention in the biopsy photography position.

FIG. 6 shows the apparatus in accordance with the invention in the biopsy photography position.

Figure 7:
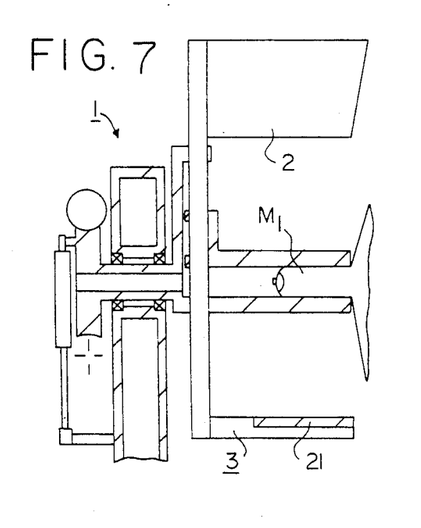
FIG. 7 shows a mammographic apparatus in accordance with the invention in the position of enlarged photography.

FIG. 7 shows the apparatus 1 in accordance with the invention in enlarged photography. In the apparatus 1 of the invention, the ratio of enlargement can be chosen freely. Typically, the ratio of enlargement in enlarged photography is 1.5:1, but in a preferred embodiment in accordance with the invention the ratio of enlargement can be chosen and adjusted continuously.

Figure 8:
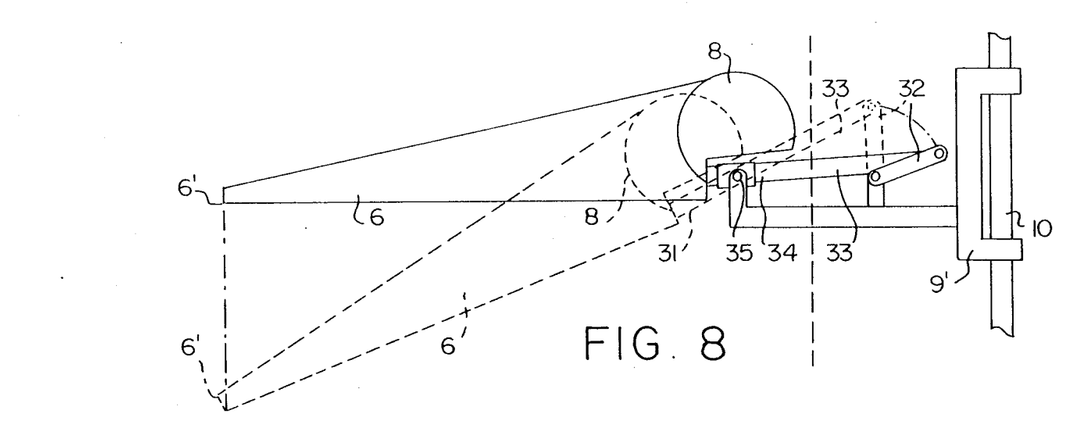
FIG. 8 is a schematical illustration of the tilting mechanism of the upper press member.

FIG. 8 is a schematical illustration of the mechanism of articulation of the upper press member 6, which mechanism permits the upper press member 6 to grasp the breast M at its root in accordance with what is explained in connection with FIG. 2, thereby leaving space for the hands of the nurse to "stretch" the breast at the initial stage of the pressing. After the upper press member 6 has pivoted against the load of the adjustable spring 31 to the normal position, i.e. substantially parallel to the lower press plate, the pressing can be continued in the same way as in the prior-art embodiments. During the pivoting movement of the press member 6, its tip 6' remains on the vertical line denoted with a dotted-dashed line in FIG. 8. The part denoted with the reference numeral 9' is a sledge that can move in the direction of pressing and that belongs to the mechanism. The parts of the articulation mechanism of the press member 6 also include a lever 32, which is connected to the casing 34 of the linear bearing by the intermediate of the rod 33, this casing being, e.g., a crosspiece, whose articulation pins are, in FIG. 8, denoted with the reference numeral 35. By means of an adjustable spring 31, the force is determined that is opposed to the pivoting of the press member to the horizontal position, i.e. the force with which the tip 6' of the press member presses the breast.

Figure 9:
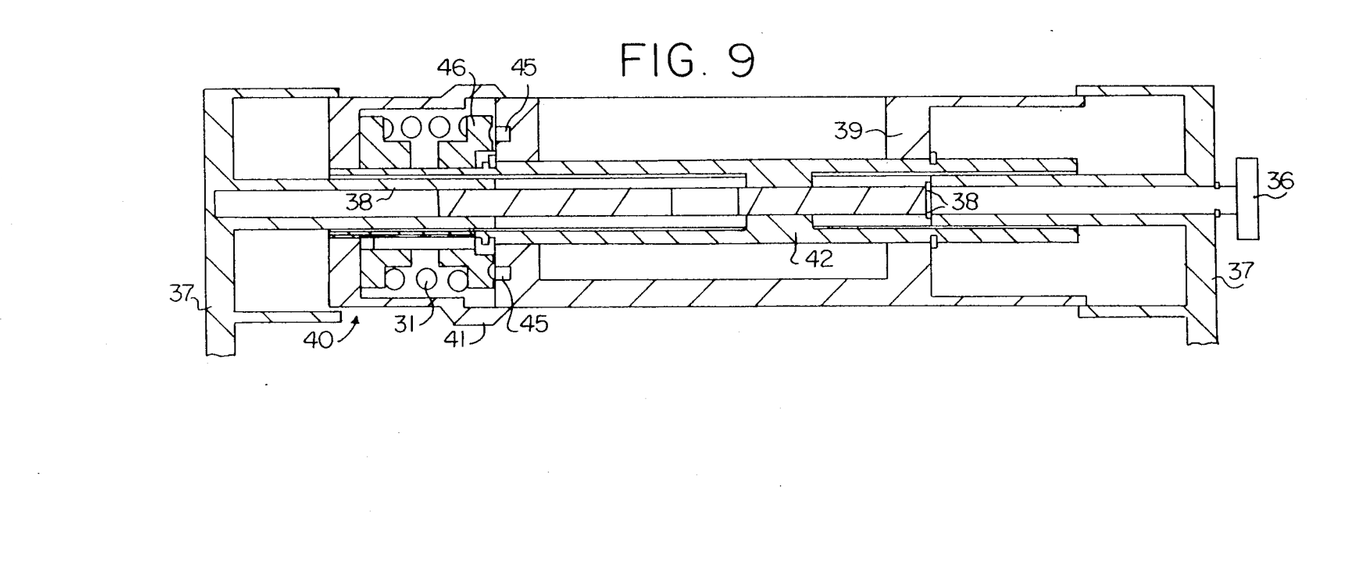
FIG. 9 illustrates the width adjustment mechanism of the apparatus.
Figure 10A:
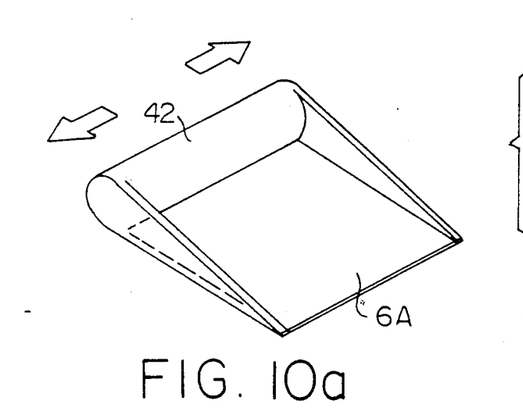
FIGS. 10a . . . 10d illustrate different exchangeable upper press plates.
Figure 10B:
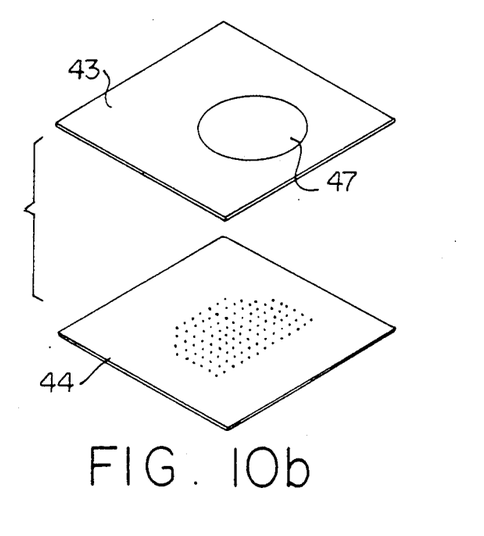
Figure 10C:
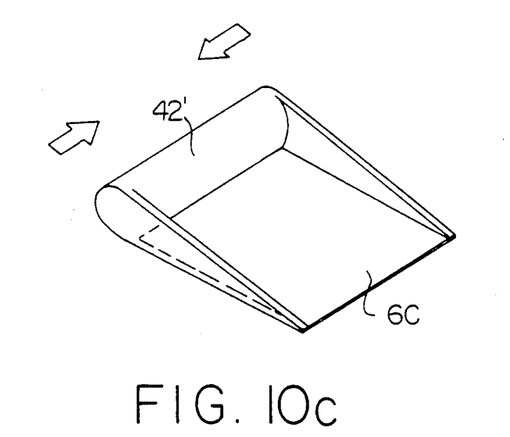
Figure 10D:
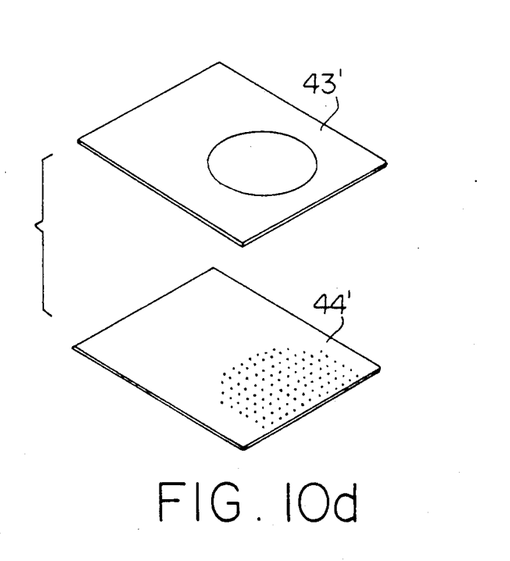

FIG. 9 illustrates the width-adjustment mechanism of the exchangeable press plates 6, which mechanism is provided with an emergency-release torque switch. The width-adjustment wheel 36 is in direct contact with the holders, e.g. brackets 37, to which the press plates 6 are attached. Between the shaft 42 and the brackets 37, there are parts 38 which permit only axial movement. The frame 39 of the width-adjustment mechanism is attached to the rods 33 shown in FIG. 8. The shaft 42 is to be non-revolving in the frame part by means of the torque switch 40, which is provided, e.g., with such a torque-adjustment wheel as is provided with recesses 46 in which the pins 45 provided on the frame part are locked when the wheel is tightened. FIGS. 10a...10d show different press plates. FIG. 10a shows a press plate 6A, e.g., for a photographing press member of a size of 30×24 cm. The press plate can be placed into a regulating mechanism 42 which can be adjusted for different widths. In FIG. 10b, the "spot" photographing press plate 6B, which is provided with an opening 47, is denoted with the numeral 43, and the biopsy press plate with the numeral 44. In FIGS. 10c and 10d, with reference numerals 42', 43',44', reference is made to the same parts as in FIGS. 10a and 10b, but for smaller, e.g. 24×18 cm, photographing press members 6C.

As has been explained heretofore, in the invention it is possible to use simple and inexpensive press plates in connection with a common mechanism 42 adjustable for different widths. Thereby substantial economies are obtained as compared with the prior art wherein generally, six different upper press members were required.

It is emphasized strongly that above only some exemplifying embodiments of the invention have been described, and the scope of the invention also includes numerous modifications of the methods and apparatuses of the invention which would be obvious to a person skilled in the art, of which only the following will be mentioned in this connection. The methods and apparatuses of the invention can also be applied in such mammography in which no X-ray film is used but in which the picture is reproduced by means of detectors which are sensitive to radiation and in themselves known, e.g. by means of electric detectors, from which an electric signal is obtained, on whose basis the picture is stored on storage media in themselves known. The definition 'film cassette or equivalent' used in the application includes such means for reproduction and storage of a picture. The scope of the invention also includes such modifications of the apparatus as have no separate lower breast holder at all but in which the film cassette or parts placed in its connection or any other, corresponding picture reproduction means referred to heretofore act as the lower holder.

In the following, the patent claims will be given, whereat the various details of the invention may show variation within the scope of the inventive idea defined in said claims.

What is claimed is:

1. Method in mammographic photography, said method comprising the steps of pressing and spreading a breast (M) to be photographed between a pair of holders (6, 7) attached to a photographing apparatus, directing a beam (R) of X-radiation from one side of said holders (6, 7) through the breast (M) placed between the holders to impinge on depicting means (21), placing said depicting means at the opposite side of the holders in relation to a source (2) of X-radiation, placing said depicting means inside a film cassette or equivalent placed in connection with the frame of the apparatus, and further comprising placing the breast M to be photographed on the top face of the lower, of said holders (6, 7), pressing the breast M to be photographed against said lower holder from a root portion thereof (J) of its upper side by means of an outer tip portion (6') of the upper, of said holders (6, 7), displacing said upper holder by pivoting it around an articulation point (8) thereat such that it becomes substantially parallel to the support plane of the lower holder (7) in a frame part (10) which is stationary relative to the source (2) of radiation and a part (3) for holding the depicting means (21), and further comprising, when the upper and lower holders (6, 7) become substantially parallel to one another, if necessary or desirable, pressing the breast further by displacing the upper holder in linear guides connected thereto so that it retains its orientation.

2. Method as claimed in claim 2, further comprising using a gas spring (18) to counterbalance a rotatable frame element (25), and placing said gas spring so as to act between a member (14) which rotates said frame element (25) and a vertical frame part (4) of the apparatus.

3. Method as claimed in claim 2, further comprising, when the ratio of enlargement of the photography is being changed, linearly displacing the source (2) of radiation and a supporting element for the depicting means (21) relative to a turnable frame element (25).

4. The method of claim 3, further comprising using a motor to linearly displace said depicting means and said supporting element.

5. Mammographic apparatus, said mammographic apparatus comprising a frame part (4), a turnable frame element (25) mounted on said frame part so as to be turnable around a horizontal axis (b—b), and comprising, connected to said frame element (25), a source (2) of radiation and depicting means (21) and further comprising a pair of holders (6, 7) for the breast to be photographed, said holders placed between the source (2) of radiation and said depicting means, which said breast holders are displaceable relative to one another so as to press the breast (M) to be photographed between said holders (6, 7), the upper one of said pair of holders (6) being placed so as to be pivotable around an axis substantially perpendicular to a central axis (a—a) of the breast, said upper holder comprising an outer tip (6') such that the breast (M) to be photographed is pressed by means of the outer tip (6') of the upper holder (6), at the initial stage of the pressing, from above the breast at a root thereof (7), and further comprising an articulation shaft connected to said upper holder such that, when the upper holder is being shifted downwards, it is pivotable around said articulation shaft such that it becomes substantially parallel to the plane of the lower (7) of said pair of holders.

6. Apparatus as claimed in claim 5, said apparatus further comprising a tube head integral to said source and an element (3) which supports the depicting means and further comprising a guide element (9) situated such that the upper holder (6) is, by means of said articulation shaft, attached to said guide element (9) and which can move in a linear manner on frame part (10) between the tube head (2) and the element (3) that supports the depicting means (21), and that said guide element (9) and said articulation shaft (8) can be displaced relative to one another.

7. Apparatus as claimed in claim 6, wherein said turnable frame element (25) comprises a vertical part, and guides (23) connected thereto, said apparatus comprises a guide-frame part (10) connected to said guides, the source (2) of radiation being attached to one end of said guide-frame part (10) and the supporting element (3) for the depicting means (21) being attached to an opposite end of said guide-frame part (10) and said apparatus further comprises, between said guide-frame part (10) and the turnable frame element (25), transfer means by means of which the source (2) of radiation and the element (3) that supports the depicting means (21) can be shifted as one unit relative to said frame element (25) and relative to the holder (7) or holders (6, 7) that press the breast (M) to be photographed.

8. Apparatus as claimed in claim 7, wherein said frame element (25) comprises a horizontal shaft and said apparatus further comprises bearings (30) on the vertical frame part (4) of the apparatus, for supporting said horizontal shaft and said apparatus further comprises a drive wheel (14) connected to said horizontal shaft, and said appartus further comprises a motor for driving said drive wheel by means of toothing on an outer rim of said motor and said apparatus further comprises a gas spring device (18) attached to said wheel such that said gas spring substantially balances the turnable frame element (25) during change of projection of photography.

9. The apparatus of claim 7, wherein said transfer means comprises a motor (12) and a transfer screw (13) connected to said motor and to said turnable frame element (25).

10. Method in mammographic photography, said method comprising the steps of:
pressing and spreading a breast (M) to be photographed between a pair of holders (6, 7) attached to a photographing apparatus;
directing a beam (R) of X-rays from one side of said pair of holders (6, 7) through the breast (M) so as to impinge upon depicting means placed at an opposite side of said holders from an X-ray source (2) of said beam of X-rays and placed within a holding means;
connecting said source (2), said holding means, and said pair of holders (6, 7) to a frame element (25) of said apparatus;
when photographing the breast (M) in different respective projections (f;g;h), turning said frame element (25) around an axis (b—b) which axis (b—b) substantially coincides with a central axis (a—a) of the breast (M) while said breast is being pressed by said holders for said different respective projections such that essentially no movement of said breast (M) and the vertical position of said apparatus is required for photographing the breast (M) in said different respective projections, and
linearly displacing the source (2) of X-rays and a supporting element for the depicting means (21) relative to said turnable frame element (25) when the ratio of enlargement of the photography is changed or when taking biopsy photographs.

11. The method of claim 10, further comprising, when the ratio of enlargement of the photography is changed, linearly displacing the source (2) of X-rays and a supporting element for the depicting means (21) relative to said turnable frame element (25).

12. The method of claim 10, further comprising using a gas spring (18) to counterbalance said rotatable frame element (25) and placing said gas spring so as to act between a member (14) which rotates said rotatable frame element (25) and a vertical frame element (4) of the apparatus.

13. The mammographic apparatus of claim 6, further comprising a tube head integral to said source and an element (3) which supports the depicting means and further comprising a guide element (9) situated such that the upper holder (6) is, by means of said articulation shaft, attached to said guide element (9) and which can move in a linear manner on the frame part (10) between the tube head (2) and the element (3) that supports the depicting means (21), and that said guide element (9) and said articulation shaft (8) can be displaced relative to one another.

14. The mammographic apparatus of claim 13, wherein said turnable frame element (25) comprises a vertical part, and guides (23) connected thereto, said apparatus comprises a guide-frame part (10) connected to said guides, the source (2) of radiation being attached to one end of said guide-frame part (10) and the supporting element (3) for the depicting means (21) being attached to the other end of said guide-frame part (10) and said apparatus further comprises, between said guide-frame part (10) and the turnable frame part (25), transfer means by means of which the source (2) of radiation and the element (3) that supports the depicting means (21) can be shifted as one unit relative to said frame part (25) and relative to the holder (7) or holders (6, 7) that press the breast (M) to be photographed.

15. The mammographic apparatus of claim 14, wherein said frame element (25) comprises a horizontal shaft and said apparatus further comprises bearings (30) on the vertical frame part (4) of the apparatus, for supporting said horizontal shaft and said apparatus further comprises a drive wheel (14) connected to said shaft, and said apparatus further comprises a motor for driving said drive wheel by means of toothing on an outer rim of said motor and said apparatus further comprises a gas spring device (18) attached to said wheel such that it substantially balances the rotatable frame part (25) during change of projection of photography.

16. Mammographic apparatus comprising:
a frame part (4);
a turnable frame element (25) mounted on said frame part so as to be turnable around a horizontal axis (b—b), said turnable frame element comprising a vertical part and guides connected thereto;
a guide-frame part (10) connected to said guides, said guide-frame part having a first end and a second end;
depicting means;
an element supporting said depicting means, said element attached to said second end of said guide frame part;
an X-ray source (2) attached to said turnable frame element said source (2) being attached to said first end of said guide-frame part (10);
a pair of holders (6, 7) respectively attached to said turnable frame element and movable to be spaced apart from each other such that a breast (M) to be photographed can be placed therebetween;
transfer means by means of which the source (2) of radiation and the element (3) that supports the depicting means (21) can be shifted as one unit relative to said frame part (25) and relative to the holder (7) or holders (6, 7) that press the breast (M) to be photographed, said transfer means located between said guide-frame part (10) and said turnable frame element (25), one of said pair of holders being affixed in a stationary position relative to said frame element such that, when said breast (M) to be photographed is impinged upon by the other of said pair of holders which is displaced so as to move closer to said one holder a central axis (a—a) of said breast substantially coincides with the axis of rotation (b—b) of the turnable frame element (25), said pair of holders (6, 7) being positioned such that, when photographing the breast (M) in different respective projections (f;g;h), turning said turnable frame element (25) around said axis of rotation (b—b) continues to result in said central axis (a—a) of said breast (M) substantially coinciding with said axis of rotation (b—b) such that essentially no movement of the breast (M) and the vertical position of said apparatus is required for photographing the breast (M) in said different respective projections.

17. The mammographic apparatus of claim 16, wherein said one of said pair of holders is the lower (7) of said pair of holders, and the other of said pair of holders is the upper (6) of said pair of holders.

18. The mammographic apparatus of claim 17, further comprising a guide element (9), an articulation shaft connected to the upper one of said pair of holders (6), such that said upper holder is, by means of said articulation shaft, attached to said guide element (9) and which can move in a linear manner on the frame part (10) between the tube head (2) and the element (3) that supports the depicting means (21), and that said guide element (9) and said articulation shaft (8) can be displaced relative to one another.

* * * * *